United States Patent [19]

Kolc et al.

[11] Patent Number: 4,517,003

[45] Date of Patent: May 14, 1985

[54] N-ACYL PHOSPHORIC TRIAMIDE UREASE INHIBITORS AND UREASE INHIBITED UREA BASED FERTILIZER COMPOSITIONS

[75] Inventors: Jaroslav F. Kolc, Randolph; Michael D. Swerdloff, Parsippany; Milorad M. Rogic, Whippany, all of N.J.; Larry L. Hendrickson, Camillus, N.Y.

[73] Assignee: Allied Corporation, Morris Township, Morris County, N.J.

[21] Appl. No.: 502,394

[22] Filed: Jun. 8, 1983

[51] Int. Cl.$^3$ ............................................. C05C 9/00
[52] U.S. Cl. ......................................... 71/28; 71/902
[58] Field of Search ............................... 71/11, 27–30, 71/902

[56] References Cited

U.S. PATENT DOCUMENTS

| 4,182,881 | 1/1980 | Bayless et al. | 546/22 |
|---|---|---|---|
| 4,222,948 | 9/1980 | Alaimo et al. | 260/397.7 R |
| 4,225,526 | 9/1980 | Alaimo et al. | 260/397.7 R |
| 4,242,325 | 12/1980 | Bayless et al. | 424/210 |

FOREIGN PATENT DOCUMENTS 830800 3/1960 United Kingdom .
1494774 12/1977 United Kingdom .

OTHER PUBLICATIONS

1978, CA, vol. 89, Abst. #89:89455K, Matzel et al.
1979, CA, vol. 90, Abst. #90:21340j, Oertal et al.
1979, CA, vol. 91, Abst. #91:122724p, Matzel et al.
1979, CA, vol. 91, Abst. #91:139619F, Heber et al.
1981, CA, vol. 94, Abst. #94:101951g, Vlek et al.
1981, CA, vol. 94, Abst. #94:139429F, Bayless et al.

*Primary Examiner*—Ferris H. Lander
*Attorney, Agent, or Firm*—Richard C. Stewart, II

[57] ABSTRACT

The invention relates to novel urease and/or nitrification inhibited fertilizer compositions containing; and methods and compositions for inhibiting urease and/or nitrification through use of a urease and/or nitrification inhibiting amount of novel phosphoric triamide compounds.

52 Claims, No Drawings

N-ACYL PHOSPHORIC TRIAMIDE UREASE INHIBITORS AND UREASE INHIBITED UREA BASED FERTILIZER COMPOSITIONS

BACKGROUND OF THE INVENTION

1. Field of the Invention

This invention relates to novel phosphoric triamide urease inhibitors and to urease inhibited urea based fertilizer compositions. More particularly, this invention relates to urease inhibited urea based fertilizer compositions which contain certain N-acyl phosphoric triamide compounds as the urease inhibitors, and methods of using such fertilizer compositions to increase plant yield, and compositions and methods of inhibiting the catalytic activity of soil urease by such N-acyl phosphoric triamide compounds.

2. The Prior Art

It is well known in the art to use urea and urea compositions in fertilizers, for application to the soil. The effective life of such fertilizers, however, is of short duration wherever microbiological activity exists in the soil to which the fertilizer is applied. This is due to the fact that urea is hydrolyzed rapidly, and nitrogen is lost in the form of ammonia, when urea is placed under or on the surface of soil which contains urease.

Urease, a crystallizable enzyme occurring in numerous bacteria and fungi, as for example *Micrococcus urease*, catalyzes the conversion of urea into ammonia and carbon dioxide. The reactions are as follows:

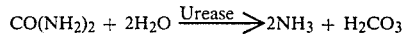

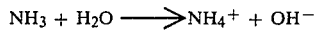

A portion of the ammonia thus formed is held by absorbing constituents of the soil and is available to plants as nutrient. However, a large amount of the ammonia may be lost to the air. A further problem resulting from the action of urease is that the rapid accumulation of ammonium species in the soil can cause damage to germinating seedlings and young plants.

One approach to the reduction of the problems resulting from the activity of soil urease toward soil applied urea is to find compounds that inhibit urease activity when applied to soils in conjunction with fertilizer urea. This approach has received considerable attention, and several classes of compounds have been used for this purpose.

For example, the prior art describes various phosphoro compounds which are useful as urease inhibitors. Illustrative of such prior art East German Pat. Nos. 142,714; 212,026; 122,177; 122,621 and 130,936, and Great Britain Pat. No. 1,494,774 which patents describe various phosphorodiamidates as urease inhibitors. U.S. Pat. No. 4,242,325 describes a method of controlling the enzymatic decomposition of urea to ammonia and carbonic acid due to the action of urease, which method comprises exposing the enzyme to certain phosphoric triamide compounds. U.S. Pat. No. 4,182,881 describes the use of certain N-(diaminophosphinyl)arylcarboxyamide compounds as inhibitors of the enzyme urease in the urinary tract. U.S. Pat. No. 4,225,526 describes the use of 8-[(4-aminophenyl)sulfonyl]amino-2-naphthalenyl phosphorodiamidate compounds as inhibitors of the enzyme urease, and U.S. Pat. No. 4,222,948 describes the use of ([(4-aminophenyl)sulfonyl]amino)phenyl phosphorodiamide compounds as inhibitors of the enzyme urease.

Still other prior art describes phosphoric triamide compounds which are useful for other purposes, for example, as flame proofing agents. For example, Great Britain Pat. No. 830,800 describes certain phosphoric triamide compounds which are useful as flame proofing agents.

SUMMARY OF THE INVENTION

In accordance with the present invention, there is provided a unique fertilizer composition comprising urea or a compound which is capable of forming urea when subjected to the use conditions of the composition, and a "urease inhibiting effective amount" of one or more N-acyl phosphoric triamide compounds of the formula:

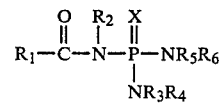

wherein:

X is oxygen or sulfur;

$R_1$ is alkyl or cycloalkyl either unsubstituted or substituted with one or more substituents selected from the group consisting of alkylamino, amino, dialkylamino, arylmercapto, halogen, mercapto, isocyano, cyano, phenoxy, isocyanato, alkylmercapto, alkoxy, nitro, quaternary ammonium radical and hydroxy;

$R_2$ is hydrogen, or cycloalkyl, alkyl or phenyl either unsubstituted or substituted with one or more substituents selected from the group consisting of halogen, phenyl, mercapto, alkyl, dialkylamino, alkylamino, trihalomethyl, cyano, phenyl, alkoxy, amino, alkylmercapto, nitro and phenoxy; and $R_3$, $R_4$, $R_5$ and $R_6$ are individually hydrogen or alkyl having from 1 to about 4 carbon atoms. In the present specification and claims, the term "phosphoric triamide compounds" is used to refer to these compounds.

Another aspect of this invention relates to a method of enhancing the yield and/or growth of plants by distributing the fertilizer composition of this invention in the "plant growth media" in which the plants are being grown within reach of the root system of the plants (hereinafter referred to as "root zone"). As used herein, the term "plant growth media" refers to various natural and artificial media which support plant growth, including but not limited to soil, potting mixtures of organic and inorganic matter and artificial media such as polyurethane foam.

Yet another aspect of this invention relates to a method of inhibiting the urease catalyzed hydrolysis of urea in some growth media or at some other situs which comprises applying a "urease inhibiting effective amount" of one or more of the aforementioned phosphoric triamide compounds to the plant growth media or said other situs prior to, after or in conjunction with the application of urea to said plant growth media or other situs. As used herein, a "urease inhibiting effective amount" is an amount of such phosphoric triamide compounds which when applied to a plant growth media or other situs, is capable of inhibiting the urease catalyzed hydrolysis of any urea in the plant growth media or at the other situs to any extent.

It has been discovered that by applying a urease inhibiting effective amount of one or more of the phosphoric triamide compounds to the plant growth media or other situs, the activity of urease in the media or at the situs is suppressed thereby preventing rapid loss of urea from the media or other situs. Furthermore, by proper distribution of the phosphoric triamide compounds in the plant growth media or other situs, the inhibition of the action of urease is effective over a prolonged period of time.

Still another more limited aspect of this invention relates to methods and compositions of inhibiting the nitrification of ammonium nitrogen which may be present in a plant growth media or other situs which comprises applying to said media or other situs a "nitrification-inhibiting effective amount" of one or more phosphoric triamide compounds of the formula:

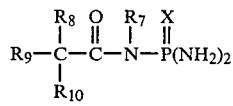

wherein:

X is oxygen or sulfur;

$R_7$ is hydrogen or alkyl having from 1 to 7 carbon atoms which alkyl may be unsubstituted or substituted with one or more halogen groups; and $R_8$, $R_9$ and $R_{10}$ are the same or different and may be $R_7$, halogen or hydrogen provided that at least one of $R_8$, $R_9$ and $R_{10}$ includes one or more halogens.

As used herein, a "nitrification inhibiting effective amount" is an amount of one or more of the aforementioned phosphoric triamide compounds which when admixed with ammonium nitrogen is sufficient to inhibit the nitrification of ammonium nitrogen to nitrate nitrogen to any extent. The ammonium nitrogen in a plant growth media may arise from the addition of one or more reduced nitrogen fertilizer to the plant growth media or formed in the media by conversion of the organic constituents in the media. The expression "reduced nitrogen fertilizers" is employed in the present specification and claims as understood in the art, and embraces both inorganic and organic nitrogenous materials containing nitrogen in the reduced state. Examples of known reduced nitrogen fertilizers include anhydrous and aqueous ammonia, inorganic ammonium salt such as ammonium phosphate, ammonium nitrate and ammonium sulfate, ammonium salts of organic acids, urea, cyanamide, guanidine nitrate, dicyandiamide, amino acids, guanyl urea sulfate, thiourea, amines, ureaform and other nitrogen-containing organic chemical fertilizers as well as protein mixtures, animal tankages, green manure, fish products, crop residues and other natural materials known to be sources of ammonium ions in plant growth media, particularly in soil. These fertilizer materials contain nitrogenous compounds in which the apparent valency or oxidation state of the nitrogen is from -3 to -1, inclusive.

DETAILED DESCRIPTION OF THE INVENTION

The application of a "urease inhibiting effective amount" and/or "nitrification inhibiting effective amount" of one or more of the above-identified phosphoric triamide compounds is essential for the practice of one embodiment of this invention. Usually, the amount of the one or more phosphoric triamide compounds required to inhibit the activity of urease is equal to that required for inhibition of nitrification. While the above-identified phosphoric triamide compounds are effective to inhibit urease activity and in the more limited embodiments to inhibit nitrification regardless of situs, the compounds are especially adapted to perform such functions in soil or some other plant growth media. Preferably, the amount of the phosphoric triamide compounds impregnated or distributed in the plant growth media is an amount which is sufficient to inhibit the urease catalyzed hydrolysis of urea present in the media at the site of application and/or sufficient to inhibit nitrification. Usually these goals can be achieved if the plant growth media is impregnated with at least about 0.01 parts of said one or more phosphoric triamide compounds per 1,000,000 parts of the plant growth media. Hereinafter, the abbreviaton of "p.p.m" designates parts of one or more phosphoric triamide compounds per million parts of soil or other plant growth media. In the preferred embodiments of this invention, the amount of said phosphoric triamide compounds impregnated in the plant growth media is from about 0.01 to about 5000 p.p.m, and in the particularly preferred embodiments of the invention is from about 0.2 to about 1000 p.p.m. on the same basis. Amongst these particularly preferred embodiments, most preferred are those embodiments in which the weight percent of said one or more phosphoric amide compounds is from about 1 to about 500 p.p.m.

Within the aforementioned limitations, the preferred amounts of the one or more phosphoric triamide compounds impregnated or distributed in the growth media are dependent upon the particular situation. Thus, in determining the amount to be employed, consideration is made not only of the treatment need, i.e., soil pH, temperature, soil type, etc., but also of the mode of application to soil. When the one or more phosphoric triamide compounds are applied in a broadcast application, the amount in p.p.m. is frequently less than in row or band application where, for a substantial depth and width within the vicinity of application, there can be a very high concentration of the one or more phosphoric triamide compounds. When application is made near the root zone of growing plants or when application is made immediately prior to seeding or transplanting, the amounts supplied are frequently at a lower rate than when application is made at the end of the growing season to prepare the soil for the following season. By dispersing very large dosages in the plant growth media, a prolonged inhibition of urease activity and/or nitrification can be obtained over a period of many months. The concentration of the one or more phosphoric triamide compounds is eventually reduced to a minimum by decomposition in the soil.

In one method for carrying out the present invention, one or more phosphoric triamide compounds are distributed throughout the plant growth media in a broadcast application, such as by spraying, dusting, distributing in irrigation water, etc. In such application, the one or more phosphoric triamide compounds are supplied in amounts sufficient to permeate the growing area of the plant growth media with an urease and/or nitrification inhibiting effective amount of such compounds. In field administration, the one or more phosphoric triamide compounds can be distributed in the plant growth media in an amount and through such cross-section of the media as to provide for the presence therein of a urease and/or nitrification inhibiting effective amount of the one or more phosphoric triamide compounds. It is usually preferred that the one or more phosphoric triamide compounds be distributed to a depth of at least two inches below the surface of the plant growth media.

In another method for carrying out the present invention, one or more phosphoric triamide compounds are administered to a plant growth media in a band or row application. In such application, administration is made with or without a carrier in amounts sufficient to supply to the soil or growth media a concentration of the one or more phosphoric triamide compounds which can be as high as 5000 p.p.m. or more. After administration with or without discing or dragging, subsequent irrigation or rainfall distributes the one or more phosphoric triamide compounds throughout the plant growth media.

In one embodiment of the present invention, the one or more phosphoric triamide compounds are distributed throughout the plant growth media prior to seeding or transplanting the desired crop plant.

In another embodiment, the soil in the root zone of growing plants is treated with the one or more phosphoric triamide compounds in an amount sufficient to inhibit the action of urease and/or to inhibit nitrification, but sublethal to plant growth. By following such practice, no adverse effect is exerted by the one or more phosphoric triamide compounds upon growth of seeds or plants. Oftentimes, it is desirable to treat the soil or plant growth media adjacent to plants, and this procedure may be carried out conveniently in side-dressing operations.

In a further embodiment, soil or plant growth media can be treated with the one or more phosphoric triamide compounds following harvest to prevent rapid loss of urea and ammonium nitrogen, and to prevent the build-up of soil urease and/or materials which promote nitrification. Such practice conserves the soil nitrogen for the following growing season. In such application, the upper limit is primarily an economic consideration.

In an additional embodiment, the soil or plant growth media is treated with the one or more phosphoric triamide compounds in conjunction with the application of urea and/or one or more reduced nitrogen fertilizers, or one or more compounds capable of forming urea or such reduced nitrogen fertilizer in situ on application to the growth media. Urea and reduced nitrogen fertilizers are well known commercially available compounds, and will not be discussed herein in detail. Illustrative of compounds which are believed to form urea on addition to the soil are water soluble formaldehyde condensation products, as for example, methylolureas, methyleneureas and mixtures thereof. These products and a method for their preparation are described in detail in U.S. Pat. No. 3,462,256. Still other useful sources of urea are water-insoluble urea formaldehyde condensation products such as ureaform. Illustrative of useful water-insoluble urea and formaldehyde condensation products are those whose preparation and use are described in detail in U.S. Pat. Nos. 3,677,736 and 4,033,745.

The present invention can be carried out by distributing the one or more phosphoric triamide compounds in an unmodified form through a plant growth medium. The present method also embraces distributing one or more such compounds as a constituent in liquid or finely divided solid compositions.

The concentration of one or more phosphoric triamide compounds in compositions to be employed for the treatment of growth media is not critical and can vary considerably provided the required dosage of effective agent is supplied to the growth media. In general, good results are obtained with liquid and/or solid compositions containing at least about 0.00001 percent by weight of the one or more phosphoric triamide compounds based on the total weight of the composition. In the preferred embodiments of the invention, the weight percent of one or more phosphoric triamide compounds is from about 0.001 to about 98 on the aforementioned basis. In the particularly preferred embodiments of the invention, the weight percent of the one or more phosphoric triamide compounds is from about 0.002 to about 50 weight percent, and in the most preferred embodiments is from about 0.01 to about 20 weight percent on the aforementioned basis. Liquid or dust compositions in which the one or more phosphoric triamide compounds are present in higher concentration can be utilized as such or can be employed as concentrate compositions to be diluted to prepare actual treating compositions.

In these compositons, the one or more phosphoric triamide compounds can be modified with one or more additaments or soil treating adjuvants including water, petroleum distillates or other liquid carriers, surface-active dispersing agents, inert finely divided solids and fertilizers, such as urea and/or reduced nitrogen fertilizers, and/or compounds capable of forming urea or such reduced nitrogen fertilizers in situ. Preferred adjuvants are surface-active dispersing agents, inert finely divided solids, and especially, reduced nitrogen fertilizers and/or urea, and their precursor compounds. These adjuvants cooperate with the one or more phosphoric triamide compounds so as to facilitate the practice of the present invention and to obtain an improved result.

The amount of urea and/or reduced nitrogen fertilizers included in the composition of this invention is not critical to the unique advantages thereof, and any amount of urea and/or such compounds or fertilizers used in conventional fertilizers can be used. Normally, the amount employed will vary widely depending on a number of factors, including the times and frequency of application. In the preferred embodiments of the invention, the total quantity of urea and/or reduced nitrogen fertilizers may vary from about 0.5 to about 95 weight percent based on the total weight of the composition and in the particularly preferred embodiments may vary from about 1 to about 50 weight percent on the same basis. In the most preferred embodiments of this invention, the quantity of urea and/or reduced nitrogen fertilizer will vary from about 3 to about 40 weight percent on the aforementioned basis.

The composition of this invention may include other optional ingredients known to those of skill in the art for inclusion in fertilizer compositions. For example, the composition may include sources of potassium, sulfur, phosphorus, boron, zinc, iron, manganese, copper, molybdenum, cobalt and like micronutrients and macronutrients which may be deficient in the soil. The composition may also include plant growth regulators, as for example auxins, cytokinins and the like, as well as pesticides such as insecticides, miticides, herbicides, nematocides and the like.

The composition of this invention which contain urea and/or reduced nitrogen fertilizers can be conveniently used in the practice of the method of this invention to increase yields in a wide variety of plants including legume crop plants and cereal crop plants. For example, the required amounts of the fertilizer composition of this invention can be applied to the soil immediately surrounding the plant, i.e., a radius up to about 20 feet, at a rate of application sufficient to obtain the desired increase in plant yield. The rate of application will depend on a number of factors, such as environmental conditions, type of crop plant and the like. The composition is usually applied at a rate of from about 5 to about 600 lbs. of urea and/or reduced nitrogen nutrient per acre in a total applied aqueous volume of from about 3 to about 1500 gallons per acre. In the preferred embodiments of the method of this invention, the composition is applied at a rate of from about 2 to about 100 pounds of urea and/or reduced nitrogen nutrient per acre in a total applied aqueous volume of from about 6 to about 250 gallons per acre, and in the particularly preferred embodiments at a rate of from about 3 to about 30 pounds per acre in a total volume of from about 9 to about 25 gallons per acre. The composition can be used in the soil or applied to the foliage of the plant, upon the seeds, or the roots of plants without injuring either the foliage, seeds or roots at any time during the growing cycle. Because of the action of the novel urease and/or nitrification inhibitors present in the composition, nitrification and/or all or a portion of the urease present at the situs of application and/or nitrification will be inhibited and greater amounts of urea and/or reduced nitrogen nutrients will be made available to the plant for longer periods of time.

Depending upon the concentration of the one or more phosphoric triamide compounds, augmented compositions can be distributed in the soil without further modification or can be considered as concentrates and subsequently diluted with additional inert carrier to produce the ultimate treating composition. The required amount of the phosphoric triamide compounds can be supplied to growth media in from about 1 to about 50 gallons of organic solvent carrier, in from about 5 to about 27,000 or more gallons of aqueous carrier or in from about 20 to about 2000 pounds of solids carrier per acre treated. When an organic solvent carrier is employed, it can be further dispersed in the above volume of aqueous liquid carrier.

Liquid compositions containing the desired amount of the one or more phosphoric triamide compounds can be prepared by dispersing the latter in one or more liquid carriers such as water or an organic solvent with or without the aid of a suitable surface active dispersing agent or emulsifying agent. Suitable organic solvents include acetone, diisobutylketone, methanol, ethanol, isopropyl alcohol, diethyl ether, toluene, methylene chloride, chlorobenzene and the petroleum distillates. The preferred organic solvents are those which are of such volatility that they leave little permanent residue in the growth media. Dispersing and emulsifying agents which can be employed in liquid compositions include condensation products of alkylene oxides with phenols and organic acids, alkyl aryl sulfonates, polyoxyalkylene derivatives or sorbitol ester, sugar esters, complex ether alcohols, mahogany soaps and the like. The surface active agents are generally employed in the amount of from 1 to 20 percent by weight based on the total weight of the composition and preferably from about 1 to about 10 weight percent on the same basis.

Solid compositions containing the active one or more phosphoric triamide compounds can be prepared by dispersing the latter in finely divided inert solid carriers such as talc, chalk, gypsum, vermiculite, bentonite and the like, fuller's earth, attapulgite and other clays, various solid detergent dispersing agents and solid fertilizer compositions. In preparing such compositions, the carrier is mechanically ground with one or more solid phosphoric triamide compounds, or wet with one or more liquid phosphoric triamide compounds or wet with a solution or dispersion of one or more solid or liquid phosphoric triamide compounds in a volatile organic solvent. Depending upon the proportions of ingredients, these compositions can be employed without further modification or be considered concentrates and subsequently further diluted with solid surface active dispersing agents, talc, chalk, gypsum or the like to obtain the desired treating composition. Furthermore, such concentrate compositions can be dispersed in water with or without added a dispersing agent or agents to prepare aqueous soil treating compositions.

While the composition and method of this invention are particularly suited for agricultural applications for prevention or inhibition of urease catalyzed hydrolysis of urea and/or nitrification, they can also be used in other applications where inhibition of the activity of urease and/or nitrification is desired. For example, such other applictions include use as urease inhibitors in animal litters, as feed additives, pharmaceutical applications, urease inhibition in mammalian urinary tracts, and the like. It should be noted that while all of the above referenced compounds exhibit some level of urease inhibiting activity, the particularly active compound employed in one application may not necessarily be useful in another application. Thus, in the selection of a particular active material for use in an application, such factors as toxicity of the material, the environment in which the material will be used, level of urease inhibition desired and the like must be considered in selecting such material.

The phosphoric triamide compounds which are employed as urease inhibitors in the composition and method of this invention are those of the formula:

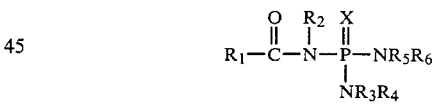

wherein:

X is sulfur or oxygen;

$R_1$ is alkyl or cycloalkyl either unsubstituted or substituted with one or more substituents selected from the group consisting of alkylamino, amino, dialkylamino, halogen, mercapto, alkylmercapto, isocyano, cyano, phenoxy, isocyanato, alkoxy, nitro, quaternary ammonium radical, and hydroxy;

$R_2$ is hydrogen or alkyl, cycloalkyl, or phenyl either substituted or unsubstituted with one or more substituents selected from the group consisting of halogens, alkyl, mercapto, trihalomethyl, cyano, alkoxy, amino, nitro, alkylamino, dialkylamino, or phenoxy, and $R_3$, $R_4$, $R_5$ and $R_6$ are the same or different and are individually hydrogen or alkyl having from 1 to about 4 carbon.

Exemplary of useful $R_1$ substituents are chloromethyl, 2,2-dichloroethyl, 2,2-dibromopropyl, 1-chloromethylethyl, 3,3- diiodobutyl, 2,2-dichloromethylethyl, 2,2,3,3-tetrachloropropyl, 2-phenoxyethyl, 2-cyanoethyl, 5-chloropentyl, 4-phenoxyhexyl, 2-iodo-2-phenylethyl, 2-phenoxypropyl, 3-mercaptobutyl, 2-(p-toluenemercapto)ethyl, 2-(phenylmercapto)propyl, 2-(ethylmercapto)propyl, hydrogen, methyl, ethyl, propyl, isopropyl, butyl, cyclohexyl, cyclopropyl, cyclobutyl, 2,2-dichlorocyclohexyl, isobutyl, pentyl, neopentyl, hexyl, 3-bromobutyl, 2-chlorocyclopropyl, 2-nitroethyl, 2-chloropentyl, 1-cyanoethyl, 2-dimethylaminopropyl, 3-methylaminobutyl, 2,3-dichlorobutyl, 1-methylmercaptoethyl, phenylmercaptomethyl, 3-nitrobutyl, 3-isocyanopropyl, 2-nitroethyl, 2-aminopropyl, 4-methoxybutyl, 2-cyano-2-chloropropyl, hydroxymethyl, 2,4-dihydroxybutyl, 3-nitropropyl, 2-phenoxyethyl, propoxymethyl, and the like.

Illustrative of useful $R_2$ substituents are methyl, ethyl, propyl, isopropyl, butyl, isobutyl, pentyl, hydrogen, chloromethyl, neopentyl, 2,2-dichloroethyl, 4-chlorophenyl, 2,2-dibromopropyl, 1-chloromethylethyl, 3-nitrophenyl, 3,3-diiodobutyl, 4-methylphenyl, 2,2-dichloropropyl, 4-cyanophenyl, 2,2,3,3-tetrachloropropyl, 3-phenoxyphenyl, 2-phenoxyethyl, 4-methylmercaptophenyl, 2-cyanoethyl, 5-chloropentyl, 4-phenoxyhexyl, 2-iodo-2-phenylethyl, 2,2-chloropropyl, 3-mercaptobutyl, 2-(p-toluenemercapto)ethyl, 2-(phenylmercapto)propyl, 2-(ethylmercapto)propyl, 2-nitroethyl, 1-cyanoethyl, 2-dimethylaminopropyl and the like.

Permissible $R_3$, $R_4$, $R_5$ and $R_6$ substituents include hydrogen, methyl, ethyl, propyl, isopropyl, butyl, isobutyl and the like.

The following compounds are illustrative of phosphoric triamide compounds within the purview of the above structural formula which can be prepared simply by selecting appropriate reactants for use in the procedures described below and which can be employed in the practice of this invention.

N-(Diaminophosphinyl)acetamide
N-(Diaminophosphinyl)butyramide
N-(Diaminophosphinyl)-3-methylhexanamide
N-(Diaminophosphinyl)-3-ethoxypropanamide
N-(Diaminophosphinyl)-N-methylacetamide
N-(Diaminophosphinyl)-N'-isopropylpentanamide
N-(Diaminophosphinyl)urea
N-(Diaminophosphinyl)-N-(4-nitrophenyl)-isobutyramide
N-(Diaminophosphinyl)2-nitroacetamide
N-(Diaminophosphinyl)-2,2-dichloropropanamide
N-(Diaminophosphinyl)-4-methylmercapto-N-ethylbutyramide
N-(Diaminophosphinyl)-3,3,3-trifluoropropanamide
N-(Diaminophosphinyl)-N',N''-dimethylacetamide
N-(Diaminophosphinyl)-N',N''-dimethyl-2,2,2-tribromoacetamide
N-(Diaminophosphinyl)-3-methyl-3-nitro-n-octanamide
N-(Diaminophosphinyl)-N'-methyl-N'-propyl-2-chlorobutyramide
N-(Diaminophosphinyl)-N-phenyl-N'-butyl-2,2-diiodopentanamide
N-(Diaminophosphinyl)-N',N'-dimethylurea
N-(Diaminophosphinyl)-2-mercaptoacetamide
N-(Diaminophosphinyl)-2,2-dichloropropanamide
N-(Diaminophosphinyl)-2,2,3-trichlorooctanamide
N-(Diaminophosphinyl)-3-methyl-2,2-dibromopentanamide
N-(Diaminophosphinyl)-2-nitro-n-butyramide
N-(Diaminophosphinyl)-2-iodoacetamide
N-(Diaminophosphinyl)-2,2-dichloro-4,5-dimethylhexanamide
N-(Diaminophosphinyl)-N'-methyl-2,2,2-trichloroacetamide
N-(Diaminophosphinyl)-N'-ethyl-2,2-dichloropropanamide
N-(Diaminophosphinyl)-N-ethyl-2-chloropentanamide
N-(Diaminophosphinyl)-N-(2'-chloroethyl)-2,2-dichloroacetamide
N-(Diaminophosphinyl)-N-phenyl-2,2-diiodobutyramide
N-(Diaminophosphinyl)-N-4-chlorophenyl-2,2-difluorohexanamide
N-(Diaminothiophosphinyl)-2,2-dichloroacetamide
N-(Diaminophosphinyl)-1-chlorocyclohexananecarboxamide
N-(Diaminophosphinyl)-2-cyanoethylisobutyramide
N-(Diaminophosphinyl)-2,2-difluoro-4-phenoxyhexanamide
N-(Diaminophosphinyl)-3-methylmercapto-2-nitropropanamide
N-(Diaminophosphinyl)-4-(N',N'-dimethylamino)-2-bromobutyramide
N-(Diaminophosphinyl)-N'-methyl-2-nitrooctanamide
N-(Diaminophosphinyl)-N-(3'-methylmercaptophenyl)-2-chloroacetamide
N-(Diaminophosphinyl)-N'-butyl-2-cyano-4-methylhexanamide
N-(Diaminophosphinyl)-N-(4-trifluoromethylphenyl)-2,2-dibromopentanamide
N-(Diaminophosphinyl)-2-ethylmercaptoisobutyramide
N-(Diaminophosphinyl)-2-phenylmercaptopropanamide
N-(Diaminothiophosphinyl)acetamide
N-(Diaminothiophosphinyl)propanamide
N-(Diaminothiophosphinyl)butyramide
N-(Diaminothiophosphinyl)-2,2,2-trichloroacetamide
N-(Diaminothiophosphinyl)-2,2,2-trifluoroacetamide
N-(Diaminothiophosphinyl)-2-fluoroacetamide
N-(Diaminothiophosphinyl)-2,2-dibromoacetamide
N-(Diaminothiophosphinyl)-2-chloroacetamide
N-(Diaminothiophosphinyl)-2-iodopropanamide
N-(Diaminothiophosphinyl)-2,2-dichlorobutyramide
N-(Diaminothiophosphinyl)-2-methylmercaptoacetamide
N-(Diaminothiophosphinyl)-2,2-dichloropropanamide
N-(Diaminothiophosphinyl)-2,2,3-trichlorooctanamide
N-(Diaminothiophosphinyl)-3-methyl-2,2-dibromopentanamide
N-(Diaminothiophosphinyl)-2-nitro-n-butyramide
N-(Diaminothiophosphinyl)-2-iodoacetamide
N-(Diaminothiophosphinyl)-2,2-dichloro-4,5-dimethylhexanamide
N-(Diaminothiophosphinyl)-N'-methyl-2,2,2-trichloroacetamide
N-(Diaminothiophosphinyl)-N'-ethyl-2,2-dichloropropanamide
N-(Diaminothiophosphinyl)-N-ethyl-2-chloropentanamide
N-(Diaminothiophosphinyl)-N-(2'-chloroethyl)-2,2-dichloroacetamide
N-(Diaminothiophosphinyl)-N-phenyl-2,2-diiodobutyramide
N-(Diaminothiophosphinyl)-N-4-chlorophenyl-2,2-difluorohexanamide
N-(Diaminothiophosphinyl)-2,2-dichloroacetamide
N-(Diaminothiophosphinyl)-1-chlorocyclohexananecarboxamide
N-(Diaminothiophosphinyl)-2-cyanoethylisobutyramide N-(Diaminothiophosphinyl)-2,2-difluoro-4-phenoxyhexanamide N-(Diaminothiophosphinyl)-3-methylmercapto-2-nitropropanamide N-(Diaminothiophosphinyl)-4-(N',N'-dimethylamino)-2-bromobutyramide N-(Diaminothiophosphinyl)-N'-methyl-2-nitrooctanamide N-(Diaminothiophosphinyl)-N-(3'-methylmercaptophenyl)-2-chloroacetamide N-(Diaminothiophosphinyl)-N'-butyl-2-cyano-4-methylhexanamide N-(Diaminothiophosphinyl)-N-(4-trifluoromethylphenyl)-2,2-dibromopentanamide N-(Diaminothiophosphinyl)-2-ethylmercaptoisobutyramide N-(Diaminothiophosphinyl)-2-phenylmercaptopropanamide Preferred for use in the practice of this invention are phosphoric triamide compounds in which:

X is oxygen;

$R_1$ is alkyl substituted with at least one substituent on the alpha, beta, or gamma carbon atoms relative to the carbonyl function;

$R_2$ is $R_1$, hydrogen, alkyl, phenyl, or phenyl substituted by 3-nitro; 4-nitro; 2,3-dimethyl; 2,4-dimethyl; 2,4,6-trimethyl; 3-trifluoromethyl; 4-cyano; 4-phenyl or 3-phenoxy; and $R_3$, $R_4$, $R_5$ and $R_6$ are the same or different and are individually hydrogen or methyl.

Particularly preferred for use in this invention are phosphoric triamide compounds in which:

X is oxygen;

$R_1$ is alkyl having from 1 to about 7 carbon atoms having at least one substituent on the alpha, beta or gamma carbon atoms relative to the carbonyl functional group, wherein the permissible substituents are selected from the group consisting of halogen, phenoxy, cyano and nitro;

$R_2$ and $R_1$ are the same or different and $R_2$ is $R_1$ or hydrogen; and $R_3$, $R_4$, $R_5$ and $R_6$ are hydrogen.

All of the compounds within the purview of the above generic formula exhibit urease inhibiting activity. A most preferred class of compounds have utility as inhibitors of nitrification in addition to urease inhibiting activity, which class of compounds are of the formula:

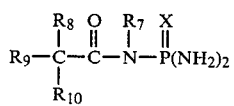

wherein:

X is oxygen or sulfur, preferably oxygen;

$R_7$ is hydrogen, phenyl, or alkyl having from 1 to 4 carbon atoms which alkyl group may be unsubstituted or substituted with one or more halogen groups; and $R_8$, $R_9$ and $R_{10}$ are the same are different and may be hydrogen, $R_7$ or halogen, provided that at least one of $R_8$, $R_9$ and $R_{10}$ includes one or more halogens.

Especially effacious compounds for use in the practice of this invention are N-(diaminophosphinyl)-2,2,2-trichloroacetamide; N-(diaminophosphinyl)-2,2,2-trifluoroacetamide; N-(daminophosphinyl)-2,2-dichloroacetamide and N-(diaminophosphinyl)-2-chloroacetamide.

Compounds for use in the practice of this invention can be prepared in accordance with the following Reaction Scheme A:

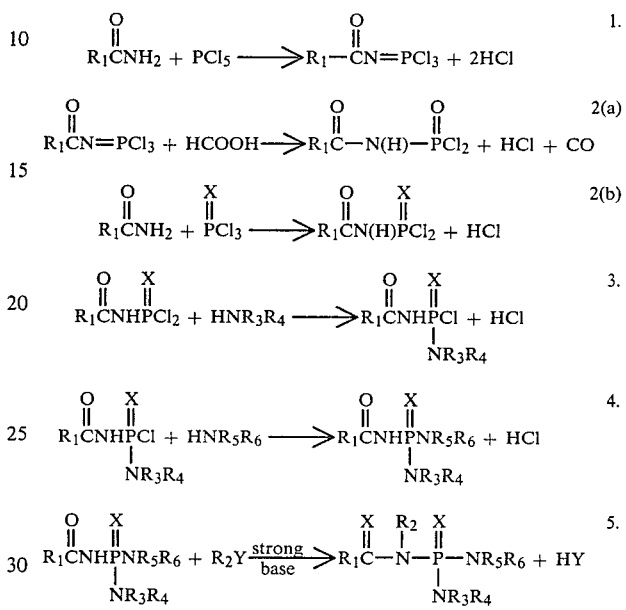

wherein $R_1$, $R_2$, $R_3$, $R_4$, $R_5$, $R_6$ and X are as defined above, and Y is a leaving group, as for example, halide, carboxylate ester, alkoxide, sulfonate ester and the like. Many of the aforementioned reactions are described in more detail in Houben-Weyl, Methoden der Organischen Chemie, Vol. XII/2, G. Thieme, Stuttgart, Germany, 1964, pp. 476–485, and references cited therein, e.g. W. Steinkopf, Chem. Ber. 41, 3571–95 (1908).

Similarly, useful compounds in which $R_2$ is other than hydrogen can be prepared in accordance with the following Reaction Scheme B, which is described in more detail in Roesky, Von H. W., et al., *Z. Anorg. Allg. Chem.*, 389, pp. 167–176 (1972):

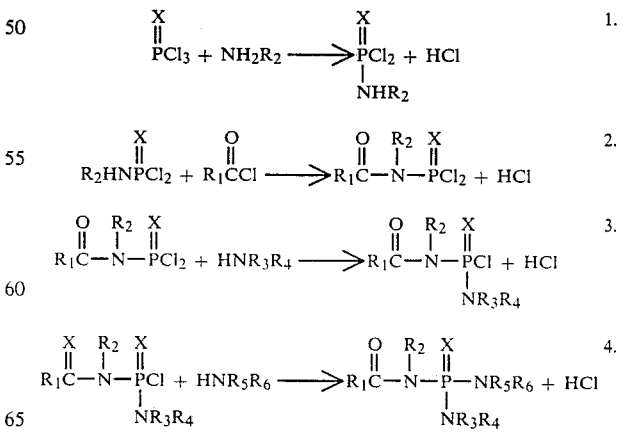

wherein $R_1$, $R_2$, $R_3$, $R_4$, $R_5$, $R_6$ and X are as described above.

Lastly, the compounds used in the practice of this invention can be prepared in accordance with the novel procedure of Reaction Scheme C below.

Reaction Scheme C

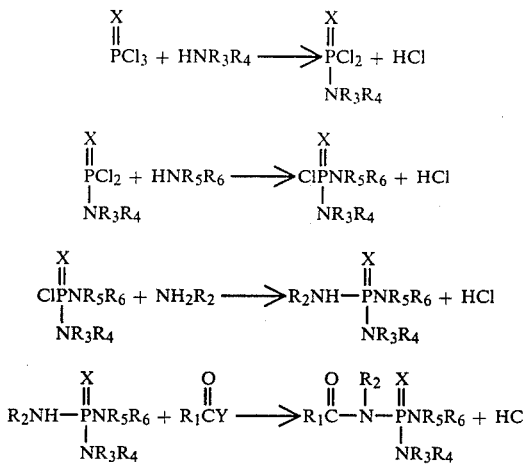

wherein $R_1$, $R_2$, $R_3$, $R_4$, $R_5$, $R_6$, X and Y are as defined hereinabove.

Briefly stated in each step of each of the multi step reaction sequences, substantially equal molar amounts or excesses of the reactants are contacted either neat or in an inert solvent. Useful inert reaction solvents include ethyl ether, carbon tetrachloride, methylene chloride, benzene, dioxane, toluene, xylene, tetrahydrofuran, methyl sulfoxide, dimethylformamide, and the like.

In the reaction steps described above, in which hydrogen chloride is a by-product, as for example, the reactions of steps 1, 2(a), 2(b), 3, 4(a) and 4(b) of Reaction Scheme A and the reactions of steps 1 through 4 of Reaction Schemes B and C, the reaction steps can be conducted in the presence of an acid acceptor. The hydrogen chloride acid acceptor employed is a basic material which can be either an inorganic or organic base. Suitable inorganic bases include alkali metal carbonates such as sodium carbonate, potassium carbonate and the like. In the preferred embodiments of the invention, organic bases are employed as the acid acceptor. Useful and preferred organic bases are tertiary amines, as for example pyridine, lutidine, 1,4-diazabicyclo[2.2.2]octane, isoquinoline, trimethylamine, quinoline, triethylamine, N-methyl pyridine and the like.

Reaction temperatures and pressures are not critical. The reaction can be conveniently carried out at a temperature of from about −30° C. to about 200° C., but is preferably carried out at a temperature of from about 0° C. to about 125° C. The reaction can be carried out at sub-atmospheric, atmospheric or super-atmospheric pressure. However, for convenience the reaction is usually carried out at atmospheric or autogeneous pressure.

The order in which the reactants are reacted indicated in the reaction scheme is for illustrative purposes only, and the order of reaction is not critical. Furthermore, the exact proportions of the reactants are not critical, some of the desired product being obtained when the reactants are employed in any proportions. However, in going to completion, the reaction consumes the reactants and the hydrogen chloride acceptor in substantially equimolar proportions, and the use of the reactants and the hydrogen chloride acceptor in such proportion is preferred, although, an excess of the acceptor can be used.

Reaction times are not critical and can be varied widely depending on such factors as the reaction temperature, reactivity of the reactants and the like. The mixture is held within the desired reaction temperature range for a period of time, conveniently from about 10 minutes to about 2 hours before cooling. Good yields are obtained with reaction times of about 30 minutes to an hour.

During those reactions in which hydrogen chloride is produced, the hydrochloride salt of the hydrogen chloride acceptor forms and may precipitate from the mixture. This salt can be removed by such conventional procedures as extraction filtration or centrifugation. The phosphoric triamide product can be separated by such conventional procedures as evaporation and purified by conventional procedures such as distillation and extraction. The product separated as described above may be employed in the control of urease in the soil in accordance with this invention or may be further purified by conventional procedures such as extraction and distillation.

The following specific examples are present to more particularly illustrate the invention.

EXAMPLE I

Preparation of N-(Diaminophosphinyl)-2,2-dichloroacetamide

A reaction mixture consisting of 2,2-dichloroacetamide (6.4 g, 50 mmol), phosphorus pentachloride (10.4 g, 50 mmol), and carbon tetrachloride (50 mL) was stirred under nitrogen while heated at reflux for 30 minutes. A clear solution resulted, which was cooled to room temperature. Formic acid (1.9 mL, 50 mmol) was added dropwise with stirring, and formation of a white precipitate was observed. The stirring was continued for 1 hour at ambient temperature. The white solid was separated by filtration, rinsed with carbon tetrachloride, and dried in vacuum over phosphorus pentoxide at ambient temperature. A yield of 10 g (82%) of N-(dichlorophosphinyl)-2,2-dichloroacetamide was obtained.

IR (IBr): 3080, 3050, 1725, 1430, 1285, 1105, 955, 885, 805, 660, 580, 505, 370 cm$^{-1}$.

N-(Dichlorophosphinyl)-2,2-dichloroacetamide (9.7 g, 39.6 mmol) was added in parts with stirring to a solution of anhydrous ammonia in ether (400 ml) saturated at 0° C. The stirring was continued after the addition for two hours. During this time the temperature of the reaction mixture was allowed to reach the room temperature. The white solid was separated by filtration, rinsed with ether, and dried in vacuum at room temperature, yield 12.0 g (97% of the theoretical amount expected for a mixture of 2 equivalents of ammonium chloride with the product).

Ammonium chloride was removed by rinsing with cold water. Final purification was achieved by crystallization from ethanol, and drying over phosphorus pentoxide in a vacuum at 80° C., mp 182°–3° C.;

IR (KBr): 3340, 3300, 3195, 1700, 1675, 1490, 1220, 1175, 1015, 890, 655 cm$^{-1}$;

$^{13}$C NMR (DMSO-$d_6$): δ 164.0 (C=O) and 66.8 ppm (CHCl$_2$); $^{31}$P NMR (DMSO-$d_6$): a single peak, 7.65 ppm downfield from 85% aqueous H$_3$PO$_4$.

Anal. Calcd for $C_2H_6Cl_2N_3O_2P$: C, 11.66; H, 2.94; Cl, 34.43; N, 20.40; P, 15.04. Found: C, 11.89; H, 2.90; Cl, 34.10; N, 20.37; P, 14.88.

EXAMPLE II

Preparation of
N-(Diaminophosphinyl)-2-chloroacetamide

The titled compound was prepared in accordance with the procedure of Example I. Using 2-chloroacetamide (7.02 g, 75 mmol), phosphorus pentachloride (15.6 g, 75 mmol) and formic acid (2.9 mL, 75 mol), were reacted to form 16.0 g of N-(dichlorophosphinyl)-2-chloroacetamide, which was reacted with anhydrous ammonia in ether to form N-(diaminophosphinyl)-2-chloroacetamide. In contrast to the behavior of N-(diaminophosphinyl)-2,2-dichloroacetamide (Example I) and N-(diaminophosphinyl)-2,2,2-trichloroacetamide (Example III), the product was very soluble even in ice-cold water, and was used for the inhibition of urease as a mixture with ammonium chloride.

EXAMPLE III

Preparation of
N-(Diaminophosphinyl)-2,2,2-trichloroacetamide

The required intermediate, namely N-(dichlorophosphinyl)-2,2,2-trichloroacetamide, was prepared according to the procedure described in A. V. Kirsanov, G. I. Derkach, Zh, Obsch. Khim., 26, 2009 (1956). Thus, from 2,2,2-trichloroacetamide (16.24 g, 0.1 mol), phosphorus pentachloride (20.83 g, 0.1 mol), and formic acid (4.6 g, 3.8 mL, 0.1 mol), were reacted to form 19.2 g of the product was obtained (65% yield), mp 150°-2° C. (lit. Kirsanov, Derkach, Obsch. Khim., see above, m.p. 148°-150° C.);

IR (KBr): 3060, 2850, 1740, 1425, 1275, 1175, 900, 810, 660, 590, 520 cm$^{-1}$, the spectrum has the same shape as the spectrum obtained from the literature (G. I. Derkach, E. S. Gubnitskaya, V. A. Schokol, A. A. Kisilenko, Zh. Obsch. Khim., 34, 82–88 (1964)).

Using the procedure of Example I, N-(dichlorophosphinyl)-2,2,2-trichloroacetamide was converted into the titled product, which was purified from the accompanying ammonium chloride by washing with ice-cold water and further crystallization from water, mp 138° C. (dec.) (lit: U.S. Pat. No. 3,317,637, mp 157°-9° C.);

IR (KBr): 3450, 3350, 3280, 3120, 1705, 1455, 1245, 1200, 1010, 895, 870, 830 cm$^{-1}$;

$^{13}$C NMR (DMSO-d$_6$): δ 161.2 (C=O), 93.2 (CCl$_3$) ppm;

$^{31}$P NMR (DMSO-d$_6$): a single peak.

Anal. Calcd. for $C_2H_5Cl_3N_3O_2P$: C, 9.99; H, 2.10; Cl, 44.24; N, 17.47; P, 13.31. Found: C, 9.89; H, 2.04; Cl, 43.60; N, 17.15; P, 12.76.

EXAMPLE IV

Preparation of
N-(Diaminophosphinyl)-2,2,2-trifluoroacetamide

N-(Diaminophosphinyl)-2,2,2-trifluoroacetamide was prepared employing the procedure of Example III by reacting 2,2,2-trifluoroacetamide (11.3 g, 0.1 mol), phosphorus pentachloride (20.83 g, 0.1 mol), and formic acid 38 mL, 0.1 mol) to form the intermediate N-(dichlorophosphinyl)-2,2,2-trifluoroacetamide, which was converted to the title compound by treatment with an ammonia-ether solution. Product yield was 12.0 g.

EXAMPLE V

Preparation of
N-(Diaminophosphinyl)-2-Cyanoacetamide

This compound was prepared in accordance with the procedure of Example I, by reacting 2-cyanoacetamide (8.4 g, 0.1 mol), phosphorus pentachloride (20.8 g, 0.1 mol), and formic acid (3.8 mL, 0.1 mol).

EXAMPLE VI

Urease Inhibition Efficacy Test

Efficacy tests were conducted to evaluate the efficacy of certain representative phosphoric triamide compounds as urease inhibitors. The inhibition tests were run in a New York soil (Cazenovia silt loam, pH 7.2). Evaluations (run in triplicate) consisted of applying 800 micrograms of the test compound in 5 mL of water and 42.8 mg of urea in 1 mL of water to 20 g of air-dry soil in a glass bottle. The bottle was capped with perforated aluminum foil and incubated at 25° C. for three days prior to extraction with 100 mL of a 2M KCl solution containing 0.5 mg of phenylmercuric acetate. The extracts were then analyzed for remaining urea using an autoanalyzer. Percent inhibition was calculated as $$\% \text{ Inhibition} = \left(1 - \frac{A-B}{A-C}\right) \times 100$$

Where A is urea recovered from unincubated sample (urea added to soil and immediately extracted); B is urea recovered from inhibited sample; and C is urea recovered from the control (uninhibited sample).

The results of these tests are set forth in the following TABLE I.

TABLE I

| | Inhibition of Soil Urease | |
|---|---|---|
| EXAMPLE | Compound | % Inhibition at at 40 ug per gram of soil |
| I | N—(Diaminophosphinyl)-2,2-dichloroacetamide | 73 |
| II | N—(Diaminophosphinyl)-2-chloroacetamide | 83 |
| III | N—(Diaminophosphinyl)-2,2,2-trichloroacetamide | 64 |
| IV | N—(Diaminophosphinyl)-2,2,2-trifluoroacetamide | 52 |

EXAMPLE VII

Efficacy tests were also conducted with jack bean urease. The procedure of Bremner (see L. A. Douglas and J. M. Bremner, Soil Biol. Biochem., 3, 859–62 (1970) and references therein) was modified by replacing the soil as the source of urease with commercial purified jack bean urease (Sigma, Type IX). The incubation then proceeds in homogeneous solution. The results are set forth in the following TABLE II:

TABLE II

| | | % Inhibition at Specific Inhibitor Concentration | | % NH$_4$Cl Con- |
|---|---|---|---|---|
| Ex. No. | Compound | $10^{-6}$ M | $10^{-7}$ M | tent |
| 1 | N—(Diaminophosphinyl)-2-Chloroacetamide | 100 | 81 | 38 |

TABLE II-continued

| Ex. No. | Compound | % Inhibition at Specific Inhibitor Concentration | | % NH4Cl Content |
|---|---|---|---|---|
| | | $10^{-6}$ M | $10^{-7}$ M | |
| 2 | N—(Diaminophosphinyl)-2,2-Dichloroacetamide | 100 | 80–100 | 0 |
| 3 | N—(Diaminophosphinyl)-2,2,2-Trichloroacetamide | 93–100 | 70 | 0 |
| 4 | N—(Diaminophosphinyl)-2-Trifluoroacetamide | 100 | 22 | 35.9 |
| 5 | N—(Diaminophosphinyl)-2-Cyanoacetamide | 56 | — | 42.1 |

EXAMPLE VIII

Several experiments were carried out to demonstrate the superior urease inhibiting activity of the N-acyl compounds of this invention as compared to that of N-acyl compounds disclosed in the prior art. The prior art compound selected for comparative testing was N-(diaminophosphinyl)-p-chlorobenzamide, and the compounds selected for use in the composition of this invention are N-(diaminophosphinyl)-2,2,2-trichloroacetamide, N-(diaminophosphinyl)-2,2-dichloroacetamide, and N-(diaminophosphinyl)-2-chloroacetamide The test procedure employed was identical to that used in Example VII. The results of the tests are set forth in the following Table III.

TABLE III

| No. | Compound | % Inhibition at Specific Inhibitor Concentrations | | |
|---|---|---|---|---|
| | | $10^{-6}$ M | $10^{-7}$ M | $10^{-8}$ M |
| 1 | N—(Diaminophosphinyl)-p-chlorobenzamide | 83 | 20 | 14 |
| 2 | N—(Diaminophosphinyl)-2,2,2-trichloroacetamide | — | 78 | 13 |
| 3 | N—(Diaminophosphinyl)-2,2-dichloroacetamide | 100 | 100 | — |
| 4 | N—(Diaminophosphinyl)-2-chloroacetamide | 100 | 50 | — |

EXAMPLE IX

Nitrification Inhibition Efficacy Test

Efficacy tests were conducted to evaluate the efficacy of certain representative phosphoric triamide compounds as nitrification inhibitors. All compounds were evaluated in Cazenovia silt loam soil (pH 7.3). The evaluations consisted of applying either simultaneously ($t_o$) or after 14 days ($t_{14}$) a solution of 6.00 mg (300 ug/g soil) of diammonium phosphate in 1 mL of water to triplicate 20 g samples of air dry soil contained in 250 mL square glass bottles that had been treated with a solution of either 0 or 0.800 mg (40 ug/g soil) of the test compound in 5 mL of water. Each bottle was capped with perforated aluminum foil, incubated for 14 days at 25° C. after diammonium phosphate application, and then extracted with 100 mL of 2M potassium chloride containing 0.5 mg (5 mg/L) of phenylmercuric acetate. Each extract was allowed to settle, and an aliquot was frozen and then analyzed for nitrate using an autoanalyzer. The percent inhibition obtained during the incubation was calculated by the formula:

$$\% \text{ Inhibition} = \left(1 - \frac{C - A}{B - A}\right) \times 100\%$$

where A is the nitrate recovered from unincubated soil before diammonium phosphate addition; B is nitrate recovered from uninhibited soil; and C is nitrate recovered from inhibited soil.

In order to demonstrate the superior nitrification inhibiting activity of the N-acylphosphoric triamides of this invention as compared to N-acylphosphoric triamides disclosed in the prior art, one of the latter, N-(diaminophosphinyl)-4-methoxybenzamide, was selected for comparative testing. The compounds selected for use in the composition of this invention are N-(diaminophosphinyl)-2,2,2-trichloroacetamide, N-(diaminophosphinyl)-2,2-dichloroacetamide, and N-(diaminophosphinyl)-2-chloroacetamide. The results of the tests are set forth in the following TABLE IV.

TABLE IV

| | Inhibition of Soil Nitrification | | |
|---|---|---|---|
| Example | Compound | % Inhibition at 40 ug per gram of soil | |
| | | $t_0$ | $t_{14}$ |
| 1 | N—(Diaminophosphinyl)-2,2,2-trichloroacetamide | 47 | 3 |
| 2 | N—(Diaminophosphinyl)-2,2-dichloroacetamide | 18 | 9 |
| 3 | N—(Diaminophosphinyl)-2-chloroacetamide | 2 | 0 |
| 4 | N—(Diaminophosphinyl)-4-methoxybenzamide | 4 | 13 |

What is claimed is:

1. A composition comprising an acceptable carrier and a urease inhibiting effective amount of one or more phosphoric triamide compounds of the formula:

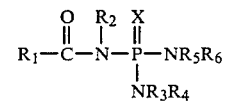

wherein:

X is oxygen or sulfur;

$R_1$ is alkyl or cycloalkyl either unsubstituted or substituted with one or more substituents selected from the group consisting of alkylamino, amino, dialkylamino, arylmercapto, alkylmercapto, isocyanato, alkoxy, nitro, halogen, mercapto, cyano, phenoxy, quaternary ammonium materials and hydroxy;

$R_2$ is hydrogen, or cycloalkyl, alkyl or phenyl either unsubstituted or substituted with one or more substituents selected from the group consisting of halo, alkyl, trihalomethyl, phenyl, cyano, alkylmercapto, mercapto, alkoxy, alkylamino, dialkylamino, amino, nitro and phenoxy; and $R_3$, $R_4$, $R_5$ and $R_6$ are individually hydrogen or alkyl having from 1 to about 4 carbon atoms.

2. A composition according to claim 1 wherein said urease inhibiting amounts is at least about 0.00001 weight percent based on the total weight of the composition.

3. A composition according to claim 2 wherein said amount is from about 0.0001 to about 98 weight percent.

4. A composition according to claim 3 wherein said amount is from about 0.002 to about 50 weight percent.

5. A composition according to claim 4 wherein said amount is from about 0.01 to about 20 weight percent.

6. A composition according to claim 1 wherein X is oxygen.

7. A composition according to claim 1 wherein $R_1$ is substituted alkyl.

8. A composition according to claim 7 wherein $R_1$ is alkyl having from 1 to about 8 carbon atoms substituted with one or more substituents on the alpha, beta of gamma carbon atoms.

9. A composition according to claim 8 wherein $R_1$ is alkyl substituted at the alpha or beta carbon atoms.

10. A composition according to claim 9 wherein $R_1$ said substituents are selected from the group consisting of halogen, nitro, or cyano.

11. A composition according to claim 10 wherein said substituents are halogens.

12. A composition according to claim 11 wherein said halogen substituents are chloro or fluoro.

13. A composition according to claim 12 wherein $R_1$ is alkyl having from 1 to about 4 carbon atoms substituted at the alpha or beta carbon atoms.

14. A composition according to claim 13 wherein $R_1$ is halogen substituted alkyl.

15. A composition according to claim 1 wherein $R_2$ is hydrogen, phenylalkyl, alkyl, cycloalkyl or phenyl.

16. A composition according to claim 15 wherein $R_2$ is hydrogen, benzyl, phenylethyl, methyl, ethyl or cyclohexyl.

17. A composition according to claim 15 wherein $R_2$ is hydrogen.

18. A composition according to claim 1 wherein $R_3$, $R_4$, $R_5$ and $R_6$ are individudally hydrogen, methyl or ethyl.

19. A composition according to claim 12 wherein $R_3$, $R_4$, $R_5$ and $R_6$ are hydrogen.

20. A composition according to claim 1 wherein $R_2$ is hydrogen.

21. A composition according to claim 1 wherein said phosphoric triamide compounds are of the formula:

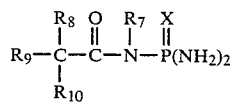

wherein:

X is oxygen or sulfur;

$R_7$ is hydrogen, cycloalkyl, phenylalkyl or alkyl;

$R_8$, $R_9$ and $R_{10}$ are the same or different and are individually $R_7$, halogen, hydrogen or alkyl substituted with one or more halogens, provided that at least one of $R_8$, $R_9$ and $R_{10}$ includes one or more halogens.

22. A composition according to claim 21 wherein $R_7$ is hydrogen or methyl.

23. A composition according to claim 22 wherein $R_7$ is hydrogen.

24. A composition according to claim 21 wherein at least one of $R_8$, $R_9$ and $R_{10}$ is halogen.

25. A composition according to claim 21 wherein X is oxygen.

26. A composition according to claim 23 wherein $R_8$, $R_9$ and $R_{10}$ are halogen, or unsubstituted or halogen substituted alkyl having from 1 to about 3 carbon atoms.

27. A composition according to claim 26 wherein $R_8$, $R_9$ and $R_{10}$ are halogen or hydrogen.

28. A composition according to claim 1 wherein said compounds are selected from the group consisting of N-(diaminophosphinyl)-2,2,2-trichloroacetamide; N-(diaminophosphinyl)-2,2,2-trifluoroacetamide; N-(diaminophosphinyl)-2,2-dichloroacetamide and N-(diaminophosphinyl)-2-chloroacetamide.

29. A method of inhibiting the urease catalyzed hydrolysis of urea at a situs which comprises distributing in said medium prior to, after or in conjunction with the application thereto of urea or a compound capable of forming urea in situ a urease inhibiting effective amount of one or more compounds of the formula:

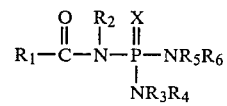

wherein:

X is oxygen or sulfur;

$R_1$ is alkyl or cycloalkyl either unsubstituted or substituted with one or more substituents selected from the group consisting of alkylamino, amino, dialkylamino, arylmercapto, alkylmercapto, isocyanato, alkoxy, nitro, halogen, mercapto, cyano, phenoxy, quaternary ammonium materials and hydroxy;

$R_2$ is hydrogen, or cycloalkyl, alkyl or phenyl either unsubstituted or substituted with one or more substituents selected from the group consisting of halogen, alkyl, trihalomethyl, phenyl, cyano, alkylmercapto, mercapto, alkoxy, alkylamino, dialkylamino, amino, nitro and phenoxy; and $R_3$, $R_4$, $R_5$ and $R_6$ are individually hydrogen or alkyl having from 1 to about 4 carbon atoms.

30. A method according to claim 29 wherein said situs is a plant growth media.

31. A method according to claim 30 wherein said amount is 0.01 ppm.

32. A method according to claim 29 wherein said amount is from about 0.01 to about 5000 ppm.

33. A method according to claim 32 wherein said amount is from about 0.2 to about 1000 ppm.

34. A method according to claim 33 wherein said amount is from about 1 to about 500 ppm.

35. An improved fertilizer composition which comprises urea and/or one or more compounds capable of forming urea in situ under the use condition of the composition and a urease inhibiting effective amount of one or more phosphoric triamide compounds of the formula:

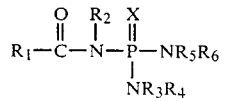

wherein:

X is oxygen or sulfur;

$R_1$ is alkyl or cycloalkyl either unsubstituted or substituted with one or more substituents selected from the group consisting of alkylamino, amino, dialkylamino, arylmercapto, alkylmercapto, isocyanato, alkoxy, nitro, halogen, mercapto, cyano, phenoxy, quaternary ammonium materials and hydroxy;

R$_2$ is hydrogen, or cycloalkyl, alkyl or phenyl either unsubstituted or substituted with one or more substituents selected from the group consisting of halogen, alkyl, trihalomethyl, phenyl, cyano, alkylmercapto, mercapto, alkoxy, alkylamino, dialkylamino, amino, nitro and phenoxy; and R$_3$, R$_4$, R$_5$ and R$_6$ are individually hydrogen or alkyl having from 1 to about 4 carbon atoms.

36. A method of enhancing plant growth and crop yield which comprises applying an effective amount of the composition according to claim 1 to a plant growth medium with the root zone of said plant.

37. A method of inhibiting the nitrification of reduced nitrogen fertilizers which comprises applying to a plant growth medium a nitrification inhibiting effective amount of one or more compounds of the formula:

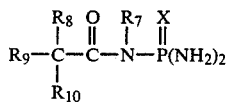

wherein:
X is oxygen or sulfur;
R$_7$ is hydrogen, cycloalkyl, phenylalkyl or alkyl;
R$_8$, R$_9$ and R$_{10}$ are the same or different and are individually R$_7$, halogen, hydrogen or alkyl substituted with one or more halogens, provided that at least one of R$_8$, R$_9$ and R$_{10}$ includes one or more halogens.

38. A composition comprising a nitrification inhibiting effective amount of one or more compounds of the formula:

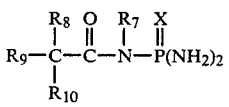

wherein:
X is oxygen or sulfur;
R$_7$ is hydrogen, cycloalkyl, phenylalkyl or alkyl;
R$_8$, R$_9$ and R$_{10}$ are the same or different and are individually R$_7$, halogen, hydrogen or alkyl substituted with one or more halogens, provided that at least one of R$_8$, R$_9$ and R$_{10}$ includes one or more halogens.

39. A composition according to claim 38 which further comprises one or more reduced nitrogen fertilizers.

40. A compound of the formula:

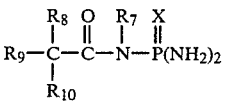

wherein:
X is oxygen or sulfur;
R$_7$ is hydrogen, cycloalkyl, phenylalkyl, alkyl; and
R$_8$, R$_9$ and R$_{10}$ are the same or different and are individually R$_7$, halogen, hydrogen, or alkyl substituted with one or more halogens, with the provision that at least one of R$_8$, R$_9$ and R$_{10}$ includes one or more halogens.

41. A compound according to claim 40 wherein R$_7$ is hydrogen.

42. A compound according to claim 41 wherein X is oxygen.

43. A compound according to claim 40 wherein R$_8$, R$_9$ and R$_{10}$ are the same or different and are halogen, hydrogen or unsubstituted or halogen substituted alkyl having from 1 to about 3 carbon atoms.

44. A compound according to claim 40 wherein:
R$_7$ is hydrogen;
R$_8$ and R$_9$ are the same or different and are hydrogen or halogen; and
R$_{10}$ is halogen.

45. A compound according to claim 40 wherein:
R$_7$, is halogen; and
R$_8$, R$_9$ and R$_{10}$ are halogen.

46. A compound according to claim 40 wherein said compound is N-(diaminophosphinyl)-2,2,2-trichloroacetamide.

47. A compound according to claim 40 wherein said compound is N-(diaminophosphinyl)-2,2-dichloroacetamide.

48. A process of preparing a compound of the formula:

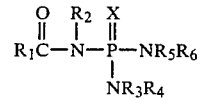

which comprises reacting a compound of the formula:

and a compound of the formula:

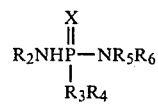

in the presence of an acid acceptor wherein:
X is oxygen or sulfur;
Y is a leaving group;
R$_1$ is alkyl or cycloalkyl either unsubstituted or substituted with one or more substituents selected from the group consisting of alkylamino, amino, dialkylamino, arylmercapto, alkylmercapto, isocyanato, alkoxy, nitro, halogen, mercapto, cyano, phenoxy, quaternary ammonium materials and hydroxy;
R$_2$ is hydrogen, or cycloalkyl, alkyl or phenyl either unsubstituted or substituted with one or more substituents selected from the group consisting of halogen, alkyl, trihalomethyl, phenyl, cyano, alkylmercapto, mercapto, alkoxy, alkylamino, dialkylamino, amino, nitro and phenoxy; and
R$_3$, R$_4$, R$_5$ and R$_6$ are individually hydrogen or alkyl having from 1 to about 4 carbon atoms.

49. A composition according to claim 1 wherein said carrier is a liquid.

50. A composition according to claim 49 wherein said liquid carrier is selected from the group consisting of water and organic liquids.

51. A composition according to claim 1 wherein said carrier is a finely divided inert solid.

52. A composition according to claim 1 wherein X is sulfur.

* * * * *